US00PP22925P2

(12) United States Plant Patent
Verschoor

(10) Patent No.: US PP22,925 P2
(45) Date of Patent: Aug. 7, 2012

(54) ***PHLOX* PLANT NAMED 'VERSWHITE'**

(50) Latin Name: *Phlox paniculata*
Varietal Denomination: Verswhite

(76) Inventor: Janus Verschoor, Haarlem (NL)

( * ) Notice: Subject to any disclaimer, the term of this patent is extended or adjusted under 35 U.S.C. 154(b) by 0 days.

(21) Appl. No.: 12/931,624

(22) Filed: Feb. 3, 2011

(51) Int. Cl.
*A01H 5/00* (2006.01)

(52) U.S. Cl. ..... Plt./320

(58) Field of Classification Search ..... Plt./320
See application file for complete search history.

*Primary Examiner* — Susan McCormick Ewoldt

(74) *Attorney, Agent, or Firm* — C. A. Whealy

(57) ABSTRACT

A new and distinct cultivar of *Phlox* plant named 'Verswhite', characterized by its upright and compact plant habit; freely flowering habit; white-colored flowers; long flowering period; and good garden performance.

2 Drawing Sheets

Botanical designation: *Phlox paniculata.*
Cultivar denomination: 'VERSWHITE'.

BACKGROUND OF THE INVENTION

The present invention relates to a new and distinct cultivar of *Phlox* plant, botanically known as *Phlox paniculata* and hereinafter referred to by the name 'Verswhite'.

The new *Phlox* plant is a product of a planned breeding program conducted by the Inventor in Haarlem, The Netherlands. The objective of the breeding program was to create new compact *Phlox* plants with attractive flower coloration.

The new *Phlox* plant originated from a cross-pollination made by the Inventor in 2005 in Haarlem, The Netherlands, of two unnamed seedling selections of *Phlox paniculata*, not patented. The new *Phlox* plant was discovered and selected by the Inventor as a single flowering plant from within the progeny of the stated cross-pollination in a controlled environment in Haarlem, The Netherlands in 2007.

Asexual reproduction of the new *Phlox* plant by cuttings in a controlled environment in Haarlem, The Netherlands since 2007 has shown that the unique features of this new *Phlox* plant are stable and reproduced true to type in successive generations.

SUMMARY OF THE INVENTION

Plants of the new *Phlox* have not been observed under all possible environmental conditions and cultural practices. The phenotype may vary somewhat with variations in environment such as temperature and light intensity without, however, any variance in genotype.

The following traits have been repeatedly observed and are determined to be the unique characteristics of 'Verswhite'. These characteristics in combination distinguish 'Verswhite' as a new and distinct *Phlox* plant:

1. Upright and compact plant habit.
2. Freely flowering habit.
3. White-colored flowers.
4. Long flowering period.
5. Good garden performance.

Plants of the new *Phlox* and the parent selections differ primarily in flower coloration. In addition, plants of the new *Phlox* have better garden performance than plants of the parent selections.

Plants of the new *Phlox* can be compared to plants of the *Phlox paniculata* 'Fujiyama', not patented. In side-by-side comparisons conducted in Haarlem, The Netherlands, plants of the new *Phlox* and 'Fujiyama' differed in the following characteristics:

1. Plants of the new *Phlox* were more compact than plants of 'Fujiyama'.
2. Plants of the new *Phlox* were sturdier than plants of 'Fujiyama'.
3. Plants of the new *Phlox* were more freely flowering than plants of 'Fujiyama'.
4. Plants of the new *Phlox* flowered for a longer period of time than plants of 'Fujiyama'.

BRIEF DESCRIPTION OF THE PHOTOGRAPHS

The accompanying colored photographs illustrate the overall appearance of the new *Phlox* plant showing the colors as true as it is reasonably possible to obtain in colored reproductions of this type. Colors in the photographs may differ slightly from the color values cited in the detailed botanical description which accurately describe the colors of the new *Phlox* plant.

The photograph on the first sheet comprises a side perspective view of a typical flowering plant of 'Verswhite' grown in a container.

The photograph at the top of the second sheet is a close-up view of a typical inflorescence of 'Verswhite'.

The photograph at the bottom of the second sheet is a close-up view of the upper surface of a typical leaf of 'Verswhite'.

DETAILED BOTANICAL DESCRIPTION

The aforementioned photographs and following observations, measurements and values describe plants grown during the late summer in an outdoor nursery in Haarlem, The Netherlands and under commercial practices. During the production of the plants, day temperatures ranged from 15° C. to 32° C. and night temperatures ranged from 8° C. to 18° C. Plants were two years old when the photographs and description were taken. In the following description, color references are made to The Royal Horticultural Society Colour Chart, 2007 Edition, except where general terms of ordinary dictionary significance are used.

Botanical classification: *Phlox paniculata* 'Verswhite'.

Parentage:

*Female, or seed, parent*.—Unnamed seedling selection of *Phlox paniculata*, not patented.

*Male, or pollen, parent*.—Unnamed seedling selection of *Phlox paniculata*, not patented.

Propagation:

*Type*.—By cuttings.

*Time to initiate roots, summer*.—About three weeks at 20° C.

*Time to produce a rooted plant, summer*.—About six weeks at 20° C.

*Root description*.—Fine, fibrous; white in color.

*Rooting habit*.—Moderate branching; medium in density.

Plant description:

*Plant form and growth habit*.—Herbaceous perennial; upright and compact plant habit; broad inverted triangle; low to moderately vigorous growth habit.

*Plant height*.—About 36.6 cm.

*Plant width* (*spread*).—About 38 cm.

*Lateral branches*.—Length: About 17.1 cm. Diameter: About 3 mm. Internode length: About 1.8 cm. Strength: Strong. Texture: Smooth, glabrous. Color: Close to 144A to 144B.

Foliage description:

*Arrangement*.—Opposite, simple.

*Length*.—About 8.6 cm.

*Width*.—About 3.1 cm.

*Shape*.—Ovate to narrowly elliptic.

*Apex*.—Narrowly acute.

*Base*.—Truncate.

*Margin*.—Entire.

*Texture, upper and lower surfaces*.—Smooth, glabrous.

*Venation pattern*.—Pinnate.

*Color*.—Developing leaves, upper surface: Close to 143A and 144A. Developing leaves, lower surface: Close to 143B to 143C. Fully expanded leaves, upper surface: Close to N137D and 147A; venation, close to 144C. Fully expanded leaves, lower surface: Close to 137B; venation, close to 144C to 144D.

*Petiole*.—Length: About 4 mm. Diameter: About 3 mm. Texture, upper and lower surfaces: Smooth, glabrous. Color, upper and lower surfaces: Close to 144C.

Flower description:

*Flower type and flowering habit*.—Single rotate and salverform flowers arranged in compound terminal panicles; flowers face upright and outwardly; panicles roughly conical in shape; freely flowering habit with about 150 flower buds and flowers developing per inflorescence.

*Fragrance*.—Moderate to strongly fragrant; sweet, pleasant.

*Natural flowering season*.—Plants begin flowering about nine months after planting; long flowering period, plants flower continuously from July through September in The Netherlands.

*Postproduction longevity*.—Flowers last about ten days on the plant; flowers not persistent.

*Flower buds*.—Height: About 2 cm. Diameter: About 5 mm. Shape: Narrowly elliptic to narrowly oblanceolate. Color: Close to 157D; towards the base, close to 145C.

*Inflorescence height*.—About 15.7 cm.

*Inflorescence diameter*.—About 11 cm.

*Flower diameter*.—About 3.2 cm.

*Flower depth*.—About 2.8 cm.

*Petals*.—Quantity per flower: Typically five in a single whorl; petals fused at the base into a narrow tube. Length: About 3.9 cm. Lobe width: About 1.8 cm. Shape: Spatulate. Apex: Obtuse. Margin: Entire. Texture, upper and lower surfaces: Smooth, glabrous. Color: When opening, upper surface: Close to NN155C; throat, close to 150B. When opening, lower surface: Close to NN155D; tube, 157A. Fully opened, upper surface: Close to NN155D; throat, close to 157C to 157D. Fully opened, lower surface: Close to NN155C; tube, 157D.

*Sepals*.—Quantity per flower: Typically five in a single whorl, fused towards the base; campanulate calyx. Length: About 9 mm. Width: About 2 mm. Shape: Lanceolate. Apex: Narrowly apiculate. Margin: Entire. Texture, upper and lower surfaces: Smooth, glabrous. Color: When opening, upper and lower surfaces: Close to 143C; towards the base and margins, close to 143D. Fully opened, upper and lower surfaces: Close to 143B and 144B; towards the base and margins, close to 143D.

*Peduncles*.—Length: About 12.1 cm. Diameter: About 3 mm. Angle: Main peduncle, erect; lateral peduncles, about 40° from vertical. Strength: Strong. Texture: Smooth, glabrous. Color: Close to 144B to 144C.

*Pedicels*.—Length: About 5 mm. Diameter: About 1 mm. Angle: About 30° from the peduncle axis. Strength: Strong. Texture: Smooth, glabrous. Color: Close to 144B to 144C.

*Reproductive organs*.—Stamens: Quantity per flower: Typically five; fused with petals in tube. Filament length: About 1.5 mm. Anther shape: Oblong. Anther length: About 2 mm. Anther color: Close to 160D. Pollen amount: Scarce. Pollen color: Close to 11D. Pistils: Quantity per flower: One. Pistil length: About 2.1 cm. Stigma shape: Three-parted. Stigma color: Close to 145D. Style length: About 2 cm. Style color: Close to 145C to 145D. Ovary color: Close to 143A.

*Seed/fruit*.—Seed and fruit development have not been observed on plants of the new *Phlox*.

Disease/pest resistance: Plants of the new *Phlox* have been noted to be relatively tolerant to Powdery Mildew. Plants of the new *Phlox* have not been noted to be resistant to pests and other pathogens common to *Phlox*.

Garden performance: Plants of the new *Phlox* have been observed to have good garden performance and tolerate rain, wind and temperatures ranging from about −10° C. to about 35° C.

It is claimed:

1. A new and distinct *Phlox* plant named 'Verswhite' as illustrated and described.

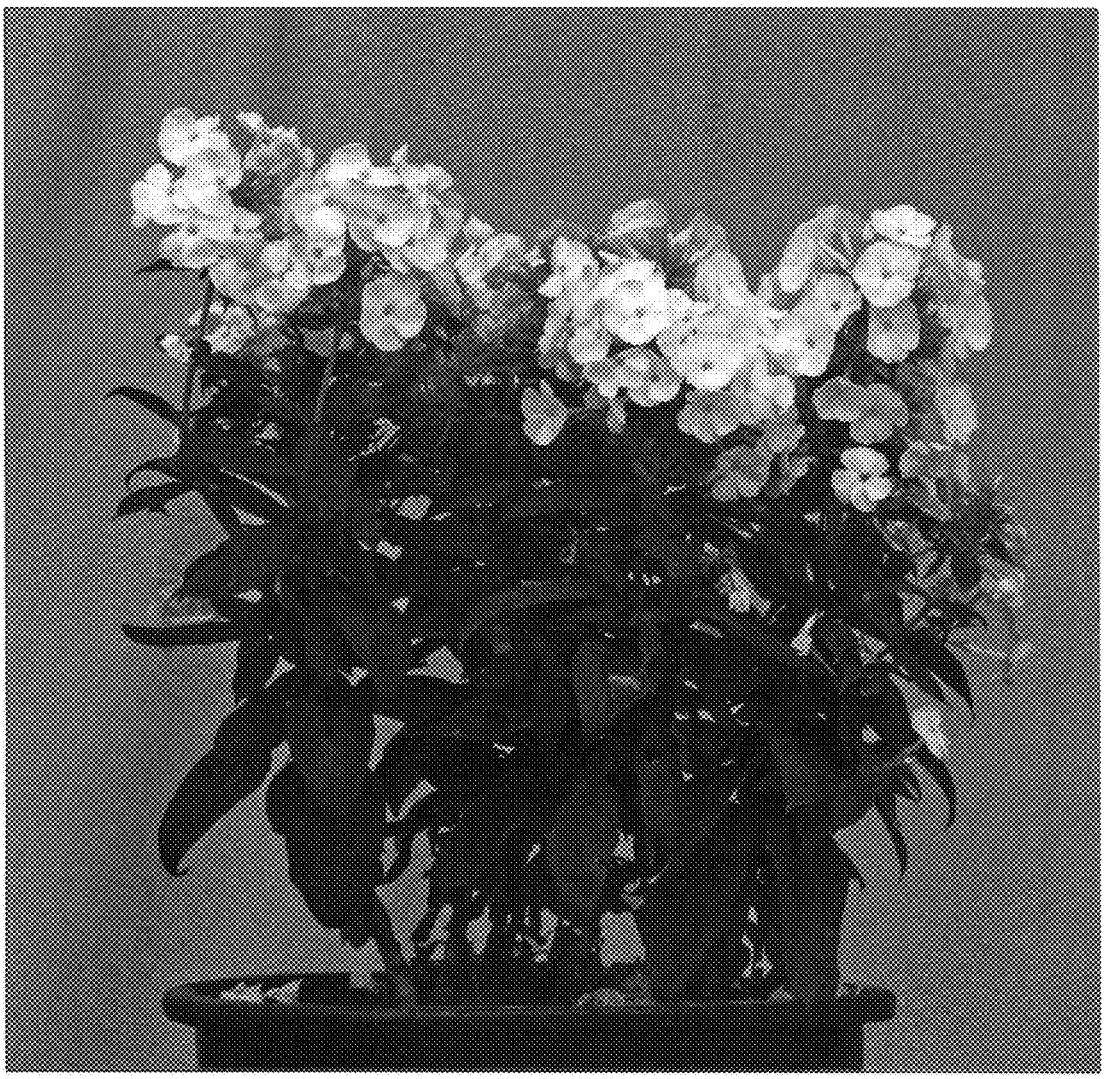

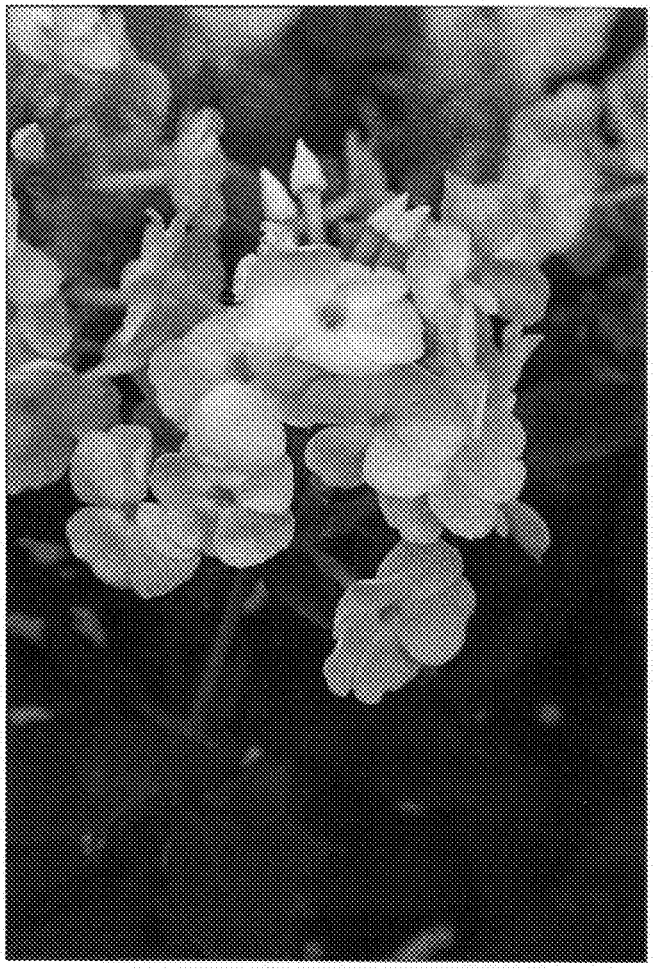
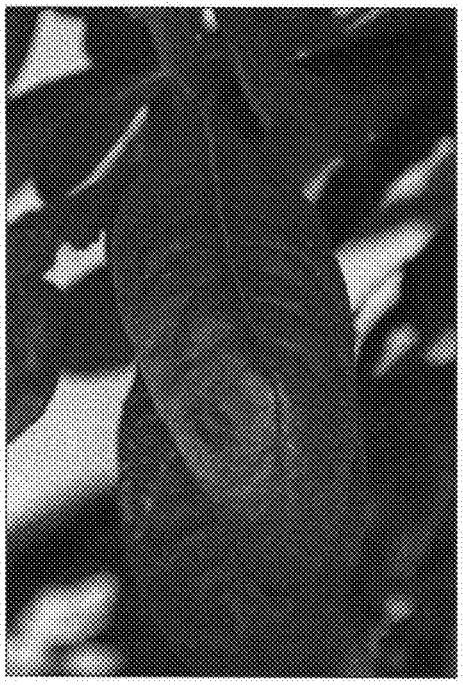

* * * * *